United States Patent
Rifai et al.

(10) Patent No.: US 11,529,049 B2
(45) Date of Patent: Dec. 20, 2022

(54) METHOD AND DEVICE FOR DETERMINING A CONTRAST SENSITIVITY THRESHOLD

(71) Applicant: Carl Zeiss Vision International GmbH, Aalen (DE)

(72) Inventors: Katharina Rifai, Tübingen (DE); Siegfried Wahl, Donzdorf (DE); Sophia Tatiyosyan, Stuttgart (DE)

(73) Assignee: Carl Zeiss Vision International GmbH, Aalen (DE)

(*) Notice: Subject to any disclaimer, the term of this patent is extended or adjusted under 35 U.S.C. 154(b) by 0 days.

(21) Appl. No.: 17/555,692

(22) Filed: Dec. 20, 2021

(65) Prior Publication Data
US 2022/0110518 A1    Apr. 14, 2022

Related U.S. Application Data

(63) Continuation of application No. PCT/EP2020/068073, filed on Jun. 26, 2020.

(30) Foreign Application Priority Data

Jun. 27, 2019 (EP) .................................. 19182861

(51) Int. Cl.
*A61B 3/02*    (2006.01)
*A61B 3/113*    (2006.01)

(52) U.S. Cl.
CPC .............. *A61B 3/022* (2013.01); *A61B 3/113* (2013.01)

(58) Field of Classification Search
CPC ........ A61B 3/022; A61B 3/113; A61B 5/1101
(Continued)

(56) References Cited

U.S. PATENT DOCUMENTS

| | | | |
|---|---|---|---|
| 7,918,558 B1* | 4/2011 | Legerton | A61B 3/113 351/246 |
| 2013/0308099 A1* | 11/2013 | Stack | A61B 5/6803 351/209 |

(Continued)

FOREIGN PATENT DOCUMENTS

| | | |
|---|---|---|
| EP | 3730037 A1 | 10/2020 |
| WO | 2017007504 A1 | 1/2017 |
| WO | 2018006013 A1 | 1/2018 |

OTHER PUBLICATIONS

Kliegl et al., "Microsaccades Uncover the Orientation of Covert Attention," Vision Research 43(9), pp. 1035 to 1045, 2003.
(Continued)

*Primary Examiner* — Mohammed A Hasan
(74) *Attorney, Agent, or Firm* — Tautz & Schuhmacher LLC; Georg Hasselmann

(57) ABSTRACT

A method and a device allow to determine the contrast sensitivity threshold of the eyes of a user in an automatic manner without requiring an experienced examiner or active attention of the user. The method includes: a) providing a dataset of track data including data of eye movements, wherein the eye movements are stimulated to elicit an optokinetic nystagmus in the eyes of the user and wherein the track data are related to a particular contrast and spatial frequency of the stimulus; b) estimating at least one velocity component of the eye movement; c) comparing the velocity component with a velocity threshold; d) comparing a fraction of the track data which exceed the velocity threshold with a fractional threshold for the dataset, which is classified as eliciting the optokinetic nystagmus at the particular contrast of the stimulus; and e) determining the contrast sensitivity threshold of the eyes of the user.

18 Claims, 3 Drawing Sheets

(58) Field of Classification Search
USPC .......................................................... 351/243
See application file for complete search history.

(56) References Cited

U.S. PATENT DOCUMENTS

| | | |
|---|---|---|
| 2015/0150443 A1 | 6/2015 | Frankfort et al. |
| 2018/0014724 A1* | 1/2018 | Wroblewski ........... G16H 10/60 |
| 2018/0055717 A1 | 3/2018 | Lange et al. |
| 2019/0167095 A1 | 6/2019 | Krueger |

OTHER PUBLICATIONS

Waddington et al., "Human optokinetic nystagmus and spatial frequency," Journal of Vision, vol. 15(13):7, pp. 1 to 16, 2015.

Dakin et al., "Similar contrast sensitivity functions measured using psychophysics and optokinetic nystagmus," Scientific Reports, 6:34514, DOI: 10.1038/srep34514, 2016.

International Search Report and Written Opinion issued in PCT/EP2020/068073, to which this application claims priority, dated Aug. 31, 2020.

International Preliminary Examination Report issued in PCT/EP2020/068073, to which this application claims priority, dated Oct. 18, 2021.

Examination report issued by the Indian Patent Office in IN202117060585, which is a counterpart hereof, dated Jun. 30, 2022 (In English and Hindi).

* cited by examiner

METHOD AND DEVICE FOR DETERMINING A CONTRAST SENSITIVITY THRESHOLD

CROSS REFERENCE TO RELATED APPLICATIONS

This application is a continuation application of international patent application PCT/EP2020/068073, filed Jun. 26, 2020, designating the United States and claiming priority from European patent application EP 19182861.5, filed Jun. 27, 2019, and the entire content of both applications is incorporated herein by reference.

TECHNICAL FIELD

The present disclosure relates to a method and a device for determining a contrast sensitivity threshold of eyes of a user and a related computer program product comprising executable instructions for performing the method. Determining the contrast sensitivity threshold is, especially, used as a common examination method in low vision. However, other kinds of applications may also be feasible.

BACKGROUND

An estimation of the contrast sensitivity, in particular of a contrast sensitivity threshold, is a common examination method in low vision which may, preferably, be executable with minimal or no cooperation of a user. Known tests, such as 'Hiding Heidi' or a LEA low-contrast symbol test, wherein gaze behavior is evaluated by an examiner in order to execute a contrast sensitivity test, have specifically been developed for users with low cooperation. Whereas the LEA low-contrast symbol test even requires verbal report, both of these tests can only be executed by a trained examiner and a cooperating user.

J. Waddington and C. M. Harris, *Human optokinetic nystagmus and spatial frequency*, Journal of Vision (2015) 15(13):7, 1-16, investigated the effect of stimulus spatial frequency on the stochastic processes of optokinetic nystagmus (OKN). Increasing the spatial frequency of suprathreshold stimuli resulted in a significant increase in velocity of compensatory slow phases with a corresponding reduction in retinal slip. However, retinal slip rarely reached values close to zero, indicating that the OKN system does not or cannot always minimize retinal slip. They deduce that OKN gain must be less than unity if extraretinal gain is lower than unity, and that the difference between retinal and extraretinal gain determines Markov properties of SP velocity. As retinal gain is reduced with stimuli of lower spatial frequency, the difference between retinal and extraretinal gain increases and the Markov properties of the system can be observed.

Experimentally, J. Waddington et al. used the following set-up. Participants sat in a chair 1 m from the middle of a flat white screen. The OKN stimulus was rear projected onto the screen. The participant's head was constrained using a chin rest. Eye movements were measured using a binocular head-mounted eye tracker which recorded horizontal eye movements. The eye tracker was calibrated for each participant by recording a voltage output of the eye tracker during fixation of targets placed at different positions on the horizontal midline of the screen. Translational OKN was elicited with a flat vertical square-wave grating, composed of alternating black and white vertical stripes moving horizontally at a fixed tangential speed, comprising a pseudorandom sequence of trials, each with a different spatial frequency, stimulus speed, or direction. Each eye was calibrated separately, and the average was computed to yield a cyclopean eye position. Eye velocity was derived from the eye position using a central difference algorithm and a Butterworth filter with zero phase. Eye acceleration was derived from the filtered eye-velocity data using a central difference algorithm. All eye movements were reviewed in a customized interactive graphical interface. Blinks were detected manually, and cycles containing blinks were marked and removed from the analysis.

S. C. Dakin and P. R. K. Turnbull, *Similar contrast sensitivity functions measured using psychophysics and optokinetic nystagmus*, Scientific Reports, 6:34514, DOI: 10.1038/srep34514, describe a system for measuring the contrast sensitivity function (CSF) using an automated analysis of the OKN, in particular, spatial-frequency (SF) band-pass noise. Quantifying the strength of the OKN in stimulus direction allows estimating the contrast sensitivity across a range of spatial frequencies. Herein, the CSFs of observers were compared with normal vision measured using both OKN and perceptual report. These approaches yielded near-identical CSFs which capture subtle intra-observer variations in visual acuity and contrast sensitivity. Trial-by-trial analysis reveals high correlation between OKN and perceptual report, being a signature of a common neural mechanism for determining stimulus direction. In contrast hereto, other conditions were observed, wherein OKN and report are significantly decorrelated as a result of a minority of observers experiencing direction-reversals that are not reflected by OKN. They conclude that a wide range of stimulus conditions exist for which OKN can provide a valid alternative means of measuring of the CSF.

Experimentally, S. C. Dakin et al. used stimuli which were presented in greyscale on a CRT monitor driven by a video-processor controlled by a personal computer. The display was viewed binocularly to minimize a contribution of any nasal and/or temporal asymmetries in optokinetic response to horizontal motion that may persist into adulthood. Display luminance was gamma calibrated using a photometer. Monocular left-eye eye movements were recorded using an eye tracker in remote mode, allowing eye tracking without use of a chin-rest. Eye movements were streamed to a personal computer. Prior to data collection, a calibration procedure was run on the eye tracker on each user, wherein every possible combination of the SFs and velocities or contrast was used. Stimulus SF, velocity, and direction were randomized across trials in order to minimize a build-up of perceptual or optokinetic aftereffects. An automated method for quantifying OKN from the output of the eye tracker was used. This method started with a raw horizontal position of the eye, then computed a first derivative of an x-position to give a horizontal velocity V of the eye, and, based on the magnitude of V, further classified the eye movements as either saccades, if their magnitude exceeds a "saccade-threshold," or tracking, if not. Based thereon, a value of an eye-movement factor which varies between 0 (i.e., velocities entirely consistent with direction opposite to stimulus), +0.5 (i.e., random velocities) and +1 (i.e., velocities entirely consistent with stimulus) was determined. Herein, a value >0.5 was scored as correct, a value <0.5 as incorrect, and a value of 0.5 as random.

European patent publication EP 3730037 A1, filed Apr. 23, 2019, discloses a method and a device for determining a refraction error of an eye of a user, wherein the method comprises presenting a sign on a screen, wherein a parameter of the sign displayed on the screen is changed; tracking of an eye movement metrics of the eye of the user depending on a change of the sign displayed on the screen; determining a point in time at which a recognition threshold arises from the eye movement metrics of the eye of the user for the sign displayed on the screen; and determining a value for the refraction error of the eye of the user from the parameter at the point in time. In a particular embodiment, eye movement metrics which are based on OKN, in particular a correlation between phase or velocity of the stimulus on the screen with the compensatory slow phases of the OKN, can be used for determining whether the user recognizes the sign displayed on the screen as a stimulus or not.

U.S. Pat. No. 7,918,558 B1 discloses a method of measuring retinal or visual pathway function which comprises stimulating optokinetic nystagmus by presenting a visual stimulus to a patient; modifying a first parameter of the visual stimulus; modifying a second parameter of the visual stimulus; and using the modified visual stimulus to determine a threshold stimulus for optokinetic nystagmus; wherein the first and second parameters are selected from a group of parameters comprising a pattern for the visual stimulus, a width of the visual stimulus, a distance between the visual stimulus and the patient, a spatial frequency of the visual stimulus, a rate of change or temporal frequency of the test face of the visual stimulus, and a contrast between elements of the visual stimulus.

WO 2018/006013 A1 discloses a system which can measure eye gaze position and detect, in near real-time, smooth eye movements that are driven by a moving stimulus. Smooth movements that match the velocity of a moving stimulus provide evidence that the subject can see the moving stimulus. The system can provide real-time feedback to the user, e.g., in the form of music, contingent on the ability of the user to perform smooth velocity-matched eye movements. The system can measure visual impairment and train visual ability both for rehabilitation and development purposes.

Problem to be Solved

In particular with respect to the disclosure of S. C. Dakin et al., see above, it is therefore an objective of the present disclosure to provide a method and a device for determining a contrast sensitivity threshold of eyes of a user and a related computer program product comprising executable instructions for performing the method which at least partially overcome the above-mentioned problems of the related art.

It is a particular objective of the present disclosure to provide an automatic contrast sensitivity test which requires neither an experienced examiner nor active attention of the user in a setting.

SUMMARY

This problem is solved by a method and a device for determining a contrast sensitivity threshold of the eyes of a user and a corresponding computer program product having executable instructions for performing a method including track data of eye movements, wherein the eye movements are stimulated by a stimulus. Exemplary embodiments, which might be realized in an isolated fashion or in any arbitrary combination, are disclosed below.

As used in the following, the terms "have," "comprise," or "include," or any arbitrary grammatical variations thereof are used in a non-exclusive way. Thus, these terms may refer to both a situation in which, besides the feature introduced by these terms, no further features are present in the entity described in this context and to a situation in which one or more further features are present. As an example, the expressions "A has B," "A comprises B," and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, as used in the following, the terms "preferably," "more preferably," "particularly," "more particularly," or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in this way with other features of the disclosure.

In a first aspect, the present disclosure relates to a method for determining a contrast sensitivity threshold of the eyes of a user. The method according to the present disclosure comprises the following steps a) to e):

a) providing a dataset of track data, wherein the track data comprise data of eye movements, wherein the eye movements are stimulated by a stimulus which is designated for eliciting an optokinetic nystagmus in the eyes of the user, wherein the track data are related to a particular contrast and a particular spatial frequency of the stimulus;

b) estimating at least one velocity component of the eye movement from the track data for the particular contrast and the particular spatial frequency of the stimulus;

c) comparing the velocity component of the eye movement for the track data with a velocity threshold;

d) further comparing a fraction of the track data which exceed the velocity threshold with a fractional threshold for the dataset, whereby the dataset which exceeds the fractional threshold is classified as eliciting the optokinetic nystagmus at the particular contrast of the stimulus; and e) determining the contrast sensitivity threshold of the eyes of the user.

Herein, the indicated steps a) to e) may, preferably, be performed in the given order, commencing with step a) and finishing with step e). However, any or all of the indicated steps may performed concurrently at least in part and/or be repeated several times. Further steps, in particular at least one of:

providing the stimulus which is designated for eliciting the optokinetic nystagmus in the eyes of the user;
tracking eye movements of the eyes of the user;
providing a contrast sensitivity curve;
providing an exportable data format;
displaying the contrast sensitivity threshold of the eyes of the user on a screen;
providing a patient history with current contrast sensitivity;
providing an alert upon change in contrast sensitivity; and
recommending future treatments, can, in addition also be performed with the present method.

Herein, the method according to the present disclosure may, particularly, be a computer-implemented method. As generally used, the term "computer-implemented method"

refers to a method which involves a programmable apparatus, in particular an evaluation unit, specifically a computer, a computer network, or a readable medium carrying a computer program, whereby at least one of the features of the method is performed by means of at least one computer program. Alternatively, the at least one computer program may be accessible by an apparatus being adapted to perform the respective method via a network, such as an in-house network or the internet. The present method can, thus, being performed on a programmable apparatus which is configured for this purpose, such as by providing a particular computer program.

According to step a), a dataset of track data is provided, wherein the dataset comprises a multitude of track data. Herein, the term "track data" refers to a plurality of data items which comprise either measured values or values which are derived from measured values, wherein the measured values are related to movements of the eyes of the user. Specifically, the measured values can be video images of the eye, such as video images having a reflex on the cornea, wherein a signal can, typically, be a relative position of the reflex to an ocular pupil, being extracted from the video images, whereas the data item can be a value, such a position or a particular pixel on a screen, which has been derived from the video images, such as by using a calibrated function. Herein, the data item can be at least one single value, such as a single value, a doublet of values, or a triplet of values, wherein the value may be a numerical value or an alphanumerical value. However, the data item may comprise further values, preferably values for a particular contrast and a particular spatial frequency of the stimulus applied for eliciting the eye movement of which the corresponding track data are recorded.

Further, the term "eye movements" refer to a motion of one or both eyes of a user which can be recorded, in particular by employing an eye tracker, wherein the eye tracker may record monocular track data or, preferably, binocular track data. Apart from spontaneous eye movements, the movement of the eyes of a user can be triggered by a stimulus, in particular by a kind of stimulus which is already known for this purpose. According to the present disclosure, the eye movements which are recorded during step a) have been stimulated by a particular kind of stimulus which is designated for eliciting an optokinetic nystagmus in the eyes of the user. As generally used, the terms "optokinetic nystagmus" or "OKN" refer to a reflexive movement of the eyes of a user which is generated as a response to a homogeneous optic flow. Herein, involuntary slow pursuit movements also denoted as "compensatory slow phases" alternate with saccadic quick phases or "saccades."

In particular for eliciting the OKN, the stimulus may exert a motion in at least one direction. In particular, a so-called "OKN drum" can be used for eliciting an optokinetic nystagmus in the eyes of the user. As generally used, the term "OKN drum" refers to a rotatable cylindrical object being covered with a pattern of alternating black and white stripes which is turned in front of the eyes of the user, specifically by rotating the cylinder clockwise or anticlockwise. In accordance with the present disclosure, the OKN drum may, preferably, be presented as virtual reality to the user, especially by using at least one of a virtual reality headset, an augmented reality (AR) overlay, or a mobile communication device, specifically a smartphone or a tablet, whereby an image of the moving OKN drum may be presented to the user. Alternatively, other kinds of stimuli may also be used in a similar fashion.

As a result thereof, a desired saccadic eye movement can be generated in which the successive execution of slow pursuit movements and saccadic quick phases can be clearly visible. Herein, the desired saccadic eye movement can be a horizontal saccadic eye movement. In a similar manner, other kinds of OKN movements, such as a vertical saccadic eye movement or a combination thereof with the horizontal saccadic eye movement, can also be generated. As generally used, the term "horizontal" refers to a direction which is provided by a connecting line which connects both eyes, in particular both pupils of the eyes, of a user. Similarly, the term "vertical" refers to a direction which is perpendicular to a horizontal direction and parallel to a direction of gravity. In an exemplary embodiment of the present disclosure, a different stimulus can, thus, be used for eliciting the saccadic motion of the eye in a horizontal direction and in a vertical direction.

Further, the track data are related to a particular contrast and a particular spatial frequency of the stimulus. Herein, various track data within the dataset can be related to a different contrast and/or a different spatial frequency of the stimulus. As generally used, the term "spatial frequency" refers to a distance in space within which a pattern is repeated, such as a stripe pattern or a noise pattern. For this purpose, the OKN drum as described above can be operated in a fashion that the cylindrical object may rotate with a particular frequency, wherein the alternating black and white stripes may have a particular width, whereby the spatial frequency of the stimulus may be defined. In addition, the alternating black and white stripes may exhibit a particular contrast with respect to each other. For further details, reference may be made to the detailed description of the embodiments below. Alternatively, other kinds of stimuli may also be used for this purpose.

In an exemplary embodiment of the present disclosure, the dataset of track data can be split into at least two subsets, wherein a particular subset comprises only track data for a particular spatial frequency or for a particular contrast of the stimulus, wherein each subset can be processed separately. As a result thereof, a velocity threshold and a fractional threshold can be estimated and validated on an independent dataset. To do so, both subsets can be labelled through visual inspection, if each phase showed an OKN or not. In a first subset, velocity and OKN threshold can be optimized in a variation procedure in order to best match the labelled data whereas, in the second subset, these thresholds can be applied, in particular, for defining an accuracy of the estimation of the contrast sensitivity by using the present method. Specifically, it could be demonstrated that the velocity threshold and the fractional threshold are universal among users, resulting in an advantage that a calibration maybe performed only once for a particular device.

In a further exemplary embodiment, a saccade filter can be applied for removing track data from the dataset which refer to the saccadic quick phases comprised by the optokinetic nystagmus. For this purpose, a saccade filter as proposed by R. Kliegl and R. Engbert, *Microsaccades Uncover the Orientation of Covert Attention*, 2003, Vision Research 43(9), pp. 1035-45 may, preferably, be used. However, further kinds of saccade filters may also be applicable. As a result thereof, only the track data which are related to the slow pursuit phases of the OKN can, exclusively, be used for estimating the velocity of the eye movement for the purposes of the present disclosure.

In a further exemplary embodiment, the dataset of the track data can be smoothed prior or, preferably, after application of the saccade filter but prior to estimating the velocity of the eye movement. For this purpose, a Savitzky-Golay filter may, preferably, be used. However, other kinds of smoothing filters may also be applicable. In this embodiment, smoothing of the data can eliminate high-frequency noise which may very likely originate from the device and which does not represent an actual eye movement.

In a further exemplary embodiment, the track data which are related to an opposite motion of the stimulus may be inverted and merged. For this purpose, it can be taken into account that the slow pursuit movements do, in general, not differ between opposite directions. In this manner the accuracy of the estimation of the contrast sensitivity can, further, be increased.

According to step b), at least one velocity component of the eye movement may be estimated from the track data, especially from the track data for the particular spatial frequency and the particular contrast of the stimulus. Preferably, the at least one velocity component of the eye movement may be estimated from the track data for each spatial frequency and for each contrast of the stimulus. As generally used, the term "velocity component" refers to a speed of a motion in a selected direction, such as in a horizontal direction or in a vertical direction. However, further kinds of components may also be feasible. As further used herein, the term "estimating" refers to a process of deriving a further value from one or more measured value by using a known rule. In accordance with the present disclosure, the track data as provided in step a) above are used for this purpose. In the particular embodiment in which a data item may be a doublet which comprises a positional value and a related temporal value, the velocity component of the eye movement can be estimated, as known by the skilled person, by a derivation of the position of the eye with respect to a temporal development of the position of the eye. This procedure may be repeated for further spatial frequencies and for further contrasts of the stimulus, preferably for each spatial frequency and each contrast of the stimulus as used during step a).

In the exemplary embodiment indicated above in which a different stimulus may be used for eliciting a motion of the eye in a horizontal direction and in a vertical direction, the velocity component can be estimated separately for a horizontal eye movement and a vertical eye movement, wherein the horizontal eye movement may follow the motion of the stimulus in the horizontal direction, and wherein the vertical eye movement may follow the motion of the stimulus in the vertical direction. In this embodiment, the different stimulus for eliciting the motion of the eye in the horizontal direction and in the vertical direction can be applied in a serial manner. However, other manners of elicitation may also be feasible, such as applying a single stimulus within a plane perpendicular to a direction of view of the user.

According to step c), the velocity component of the eye movement for the track data, especially for the track data related to the particular spatial frequency and the particular contrast of the stimulus, is compared with a velocity threshold. As generally used, the term "velocity threshold" refers to a particular velocity to which the velocity component of the eye movement is compared with, specifically in a fashion to estimate which of the velocity component and the velocity threshold exhibits a larger value.

Herein a single velocity threshold may, preferably, be applicable for each kind of velocity component. However, in the embodiment indicated above in which a different stimulus is used for eliciting a motion of the eye in a horizontal direction and in a vertical direction and in which the velocity component can be estimated separately for a horizontal eye movement and a vertical eye movement, a separate horizontal velocity threshold can be used for comparison of the horizontal eye movement, and a separate vertical velocity threshold can, further, be used for comparison of the vertical eye movement. For further details, reference may be made to the description of the embodiments below.

According to step d), a fraction of the track data which exceeds the velocity threshold is compared with a fractional threshold for the dataset in a fashion that the dataset which exceeds the fractional threshold is classified as eliciting the optokinetic nystagmus in the eyes of the user at the particular contrast of the stimulus. As used herein, the term "fractional threshold" refers to a value which indicates a fraction, in particular a value between 10% and 90%, preferably between 30% and 70%, more preferred between 40% and 60%. By way of example, in a case in which the fractional threshold may be 48% while 60% of the track data within the dataset of track data may exceed the velocity threshold as indicated above, the corresponding dataset can be classified as eliciting the optokinetic nystagmus in the eyes of the user at the particular contrast of the stimulus.

Consequently, applying both the velocity threshold and the fractional threshold to the dataset of track data in the fashion according to the method as disclosed herein allows determining the contrast sensitivity threshold of the eyes of the user according to step e), in particular by identifying a smallest value for the contrast which elicits the optokinetic nystagmus. As generally used, the term "determining" relates to a process of generating at least one representative result, such as a plurality of representative results, in particular by applying the method according to the present disclosure. As further generally used, the term "contrast sensitivity" refers to a measure of an ability of at least one eye of a user to discern between luminances of different levels in a stimulus. Moreover, the term "contrast sensitivity threshold" can be defined as an inverse of a Michelson contrast at threshold, wherein the Michelson contrast estimates are based on image grayscale values which may be obtained by patterns in which both bright and dark features are equivalent and take up similar fractions of the area, such as black and white stripes in the OKN drum.

Herein, the dataset of the track data can, preferably, already be classified as eliciting the optokinetic nystagmus if the dataset has been classified before as eliciting the optokinetic nystagmus only for the horizontal eye movement or only for the vertical eye movement. As a result thereof, comparing only the track data for the horizontal eye movement with the horizontal velocity threshold or only the track data for the vertical eye movement with the vertical velocity threshold and using the velocity threshold according to step d) may already allow classifying the respective dataset of track data as eliciting the optokinetic nystagmus in the eyes of the user at the particular contrast of the stimulus.

Surprisingly, it could be verified as demonstrated below in more detail, that both the velocity threshold and the fractional threshold can be dataset as independent from the user of whose eyes the contrast sensitivity threshold is determined. Rather, both the velocity threshold and the fractional threshold can be estimated in a calibration process in which the method according to the present disclosure is performed with different users in the same manner, whereby, the same kind of stimulus and the same kind of equipment, notably the same kind of screen and the same kind of eye tracker, are used, in particular. As a result thereof, the method of the present disclosure allows determining the contrast sensitivity threshold of the eyes of any user who applies the calibrated process.

Not wishing to be bound by theory, the fractional threshold as proposed by the present method can resolve inaccuracies which may, automatically, be generated by the eye tracker being used for providing the dataset of track data for step a) with respect to an actual position of the eye of the user. As a consequence of these inaccuracies, artificial velocities can be estimated during step b) from inaccurately determined eye positions. Herein, the artificial velocities may, in general, increase with increasing noise inevitably generated by the eye tracker. The fractional threshold can, thus, be considered as a measure for an artificial level eliciting the optokinetic nystagmus in the eyes of the user. Taking into account these inaccuracies in the form of the fractional threshold, thus, allows considerably increasing the accuracy of the determination of the contrast sensitivity threshold.

In particular contrast to S. C. Dakin et al. as referenced above, according to the present disclosure a velocity component is determined for a particular item of track data and it is, then, checked whether the velocity component for this particular item of track data exceeds the velocity threshold. It is, then, further determined in how many of the track data items in the dataset the corresponding velocity component exceeds the velocity threshold, whereby the fraction of such track data items in the dataset that meet this condition is obtained. Then, it is checked whether this fraction exceeds the fractional threshold. In contrast hereto, in S. C. Dakin et al. the horizontal velocity of the eye is estimated. Then, it is checked, in further accordance with step c), whether this velocity exceeds a "saccade-threshold" which defines a particular threshold for the eye velocity. Then, a total distance Do travelled by the eye that was consistent with the OKN in the direction Θ is determined. Using this value for the totally traveled distance Do, a ratio Co is determined which indicates a fractional value of the total eye movement which is consistent with the OKN. Consequently, this value for the ratio Co differs from the definition of the fractional threshold. As a result, the present method already allows determining whether a particular dataset can be classified as eliciting the optokinetic nystagmus at the particular contrast of the stimulus or not, wherein neither a determination of any distances nor a computation of any ratios of distances is required. Further, the requirement by S. C. Dakin et al that the analysis of the eye movements must accommodate known dynamic properties of OKN, in particular a latency preceding its initiation, which requires compensating a delay before the OKN switches to reflect the change in stimulus direction, can be avoided here.

In a further aspect, the present disclosure refers to a computer program product which comprises executable instructions for performing the method for determining a contrast sensitivity threshold of eyes of a user according to the present disclosure. For this purpose, a computer program may comprise instructions provided by means of a computer program code which are capable of performing any or all of the steps of the methods as described elsewhere herein and, thus, to establish determining the contrast sensitivity threshold of the eyes of a user when implemented on a computer or a data processing device.

The computer program code may be provided on a data storage medium or a separate device such as an optical storage medium, e.g., on a compact disc, directly on a computer or a data processing device, in particular a mobile communication device, specifically a smartphone or a tablet, or via a network, such as an in-house network or the internet.

For further details concerning the computer program product, reference may be made to the method according to the present disclosure as disclosed elsewhere herein.

In a further aspect, the present disclosure relates to a device for determining a contrast sensitivity threshold of eyes of a user. Herein, the device comprises
  a screen for displaying a stimulus, wherein the stimulus which is designated for eliciting an optokinetic nystagmus in the eyes of the user;
  an eye tracker, wherein the eye tracker is designated for recording a movement of the eyes of the user; and
  an evaluation unit, wherein the evaluation unit is designated for performing the method for determining a contrast sensitivity threshold of the eyes of the user as described elsewhere herein.

In an exemplary embodiment of the present disclosure, the screen, the eye tracker, and the evaluation unit may be integrated in a virtual reality headset. Alternatively, the evaluation unit can partially be comprised by a mobile communication device, specifically a smartphone or a tablet, which is in communication with the virtual reality headset. As generally used, the term "virtual reality headset" refers to a head-mounted device which is designated for providing virtual reality for the user who wears the virtual reality headset. In general, the virtual reality headset comprises a stereoscopic head-mounted display which may be capable of providing separate images for each eye; stereo sound; a head motion tracking sensors, such as a gyroscope, an accelerometer, or a structured light system; and an eye tracking sensor.

In another exemplary embodiment, the screen, the eye tracker and the evaluation unit may be comprised by a mobile communication device, specifically a smartphone or a tablet. As further generally used, the term "mobile communication device" refers to a mobile communication device which comprises a mobile operating system being designated for facilitating a use of software, internet, and multimedia functionalities. In this embodiment, the mobile communication device may, thus, be configured to provide the functionalities of the screen, the eye tracker and the evaluation unit as described above or below. In particular, the mobile communication device may, for this purpose, comprise at least one sensor, in particular, selected from a gyroscope, an accelerometer, a proximity sensor, a magnetometer, or a barometer, and may support wireless communications protocols such as Wi-Fi or Bluetooth.

In a further preferred alternative embodiment, the screen and the eye tracker may be integrated in smart glasses whereas the evaluation unit can be comprised by a mobile communication device being in communication with the smart glasses. As generally used, the term "smart glasses" refers to glasses which are wearable by a user and which are designed for superimposing information onto a field of view of the user. Further, the smart glasses may be designated for changing optical properties when worn by the user. For these purposes, embedded wireless glasses with a transparent heads-up display or an augmented reality (AR) overlay may be used which, on one hand, allow a usual visual reception by the user and, on the other hand, are designed for projecting digital images provided by integrated applications.

Alternatively or in addition, further embodiments with respect to the device according to the present disclosure are conceivable.

With respect to the related art, the method and the device according to the present disclosure exhibit the following advantages. In particular, the method and the device allow automatic estimation of the contrast sensitivity requiring only little cooperation of the user within less than 5, preferably less than 4, preferably less than 3 minutes, of duration of the method. Consequently, they provide a powerful tool for determining the contrast sensitivity testing which incorporates easy applicability and short test durations. Herein, an implementation of the hardware in a single or in two cooperating devices as well as an incorporation of the software is designed for making the tool applicable even for untrained users or personnel. Furthermore, the present tool for determining the contrast sensitivity is adapted for providing an objective measure, wherein measurements from different performances can easily be stored and compared, thus allowing an assessment of long-term trends in the eyes of a user. Further, the present tool could even be applied at home as a screening tool, potentially implemented even in augmented reality. In this fashion, the present disclosure can complement medical care in progressing diseases as a screening tool by which the contrast sensitivity may be estimated on a much more regular basis compared to regular visits. As a result thereof, stepwise degradation of visual function of a user can be detected earlier and treated much more efficiently.

Summarizing, the following exemplary embodiments set forth in the Clauses below are particularly typical within the scope of the present disclosure:

Clause 1. A method for determining a contrast sensitivity threshold of eyes of a user, the method comprising the following steps:
  a) providing a dataset of track data, wherein the track data comprise data of eye movements, wherein the eye movements are stimulated by a stimulus which is designated for eliciting an optokinetic nystagmus in the eyes of the user, wherein the track data are related to a particular contrast and a particular spatial frequency of the stimulus;
  b) estimating at least one velocity component of the eye movement from the track data for the particular contrast and the particular spatial frequency of the stimulus;
  c) comparing the velocity component of the eye movement for the track data with a velocity threshold;
  d) further comparing a fraction of the track data which exceed the velocity threshold with a fractional threshold for the dataset, whereby the dataset which exceeds the fractional threshold is classified as eliciting the optokinetic nystagmus at the particular contrast of the stimulus; and
  e) determining the contrast sensitivity threshold of the eyes of the user.

Clause 2. The method according to the preceding Clause, wherein the velocity threshold and the fractional threshold are independent from the user.

Clause 3. The method according to any one of the preceding Clauses, wherein the velocity threshold and the fractional threshold is dependent from an eye tracker being used for recording the track data.

Clause 4. The method according to any one of the preceding Clauses, wherein the velocity threshold and the fractional threshold are estimated in a calibration process.

Clause 5. The method according to the preceding Clause, wherein the method is performed during the calibration process with at least two different users in the same manner.

Clause 6. The method according to any one of the two preceding Clauses, wherein the same contrasts and the same spatial frequencies of the same stimulus are used.

Clause 7. The method according to any one of the preceding Clauses, wherein the dataset is split into at least two subsets for the contrast and the spatial frequency of the stimulus, wherein each subset is processed separately.

Clause 8. The method according to any one of the preceding Clauses, wherein a saccade filter is applied for removing track data from the dataset which refer to saccadic quick phases comprised by the optokinetic nystagmus.

Clause 9. The method according to any one of the preceding Clauses, wherein the dataset is smoothed.

Clause 10. The method according to the preceding Clause, wherein a Savitzky-Golay filter is used.

Clause 11. The method according to any one of the preceding Clauses, wherein the stimulus exerts a motion in at least one direction.

Clause 12. The method according to the preceding Clause, wherein an OKN drum is used or wherein an image of the moving OKN drum is presented to the user as virtual reality.

Clause 13. The method according to the preceding Clause, wherein the moving OKN drum is presented to the user as virtual reality by using at least one of a virtual reality headset, an augmented reality (AR) overlay, or a mobile communication device.

Clause 14. The method according to the preceding Clause, wherein the OKN drum is a rotatable cylindrical object being covered with a pattern of alternating black and white stripes which are turned in front of the eyes of the user.

Clause 15. The method according to the preceding Clause, wherein the cylinder of the OKN drum is rotated clockwise or anticlockwise.

Clause 16. The method according to any one of the preceding Clauses, wherein a different stimulus is used for a motion in a horizontal direction and in a vertical direction.

Clause 17. The method according to any one of the preceding Clauses, wherein the velocity component is estimated separately for a horizontal eye movement and a vertical eye movement.

Clause 18. The method according to the preceding Clause, wherein the horizontal eye movement follows the motion of the stimulus in the horizontal direction.

Clause 19. The method according to any one of the two preceding Clauses, wherein the vertical eye movement follows the motion of the stimulus in the vertical direction.

Clause 20. The method according to any one of the preceding Clauses, wherein the track data which are related to an opposite motion of the stimulus are inverted and merged.

Clause 21. The method according to any one of the preceding Clauses, wherein the dataset is classified as eliciting the optokinetic nystagmus if the dataset has been classified as eliciting the optokinetic nystagmus for the horizontal eye movement or for the vertical eye movement.

Clause 22. The method according to any one of the preceding Clauses, wherein the contrast sensitivity threshold of the eyes of the user is determined by identifying a smallest value for the contrast eliciting the optokinetic nystagmus.

Clause 23. The method according to any one of the preceding Clauses, wherein the contrast sensitivity threshold is determined as a relative comparison between different contrast sensitivity thresholds.

Clause 24. The method according to any one of the preceding Clauses, wherein a luminance level of the stimulus is measured.

Clause 25. The method according to the preceding Clause, wherein the luminance level of the stimulus is measured by using a luminance sensor.

Clause 26. The method according to any one of the two preceding Clauses, wherein the contrast sensitivity threshold is determined as an absolute contrast sensitivity threshold by considering a measured value for the luminance level of the stimulus.

Clause 27. A computer program product comprising executable instructions for performing a method for determining a contrast sensitivity threshold of eyes of a user according to any one of the preceding Clauses.

Clause 28. A device for device for determining a contrast sensitivity threshold of eyes of a user, the device comprising
- a screen for displaying a stimulus, wherein the stimulus is designated for eliciting an optokinetic nystagmus in the eyes of the user;
- an eye tracker, wherein the eye tracker is designated for recording a movement of the eyes of the user; and
- an evaluation unit, wherein the evaluation unit is designated for performing the method according to any one of the preceding Clauses referring to the method.

Clause 29. The device according to the preceding Clause, wherein the screen and the eye tracker are integrated in at least one of a virtual reality headset, smart glasses, or a mobile communication device.

Clause 30. The device according to any one of the preceding Clauses referring to the device, wherein the evaluation unit is comprised by at least one of the virtual reality headset and a mobile communication device.

Clause 31. The device according to the preceding Clause, wherein the mobile communication device is selected from a smartphone or a tablet.

Clause 32. The device according to any one of the preceding Clauses referring to the device, further comprising a luminance sensor.

BRIEF DESCRIPTION OF THE DRAWINGS

The disclosure will now be described with reference to the drawings wherein.

DESCRIPTION OF EXEMPLARY EMBODIMENTS

Further optional features and embodiments of the present disclosure are disclosed in more detail in the subsequent description of preferred embodiments, preferably in conjunction with the dependent claims. Therein, the respective optional features may be realized in an isolated fashion as well as in any arbitrary feasible combination, as the skilled person will realize. It is emphasized here that the scope of the disclosure is not restricted by the preferred embodiments.

Figure 1:
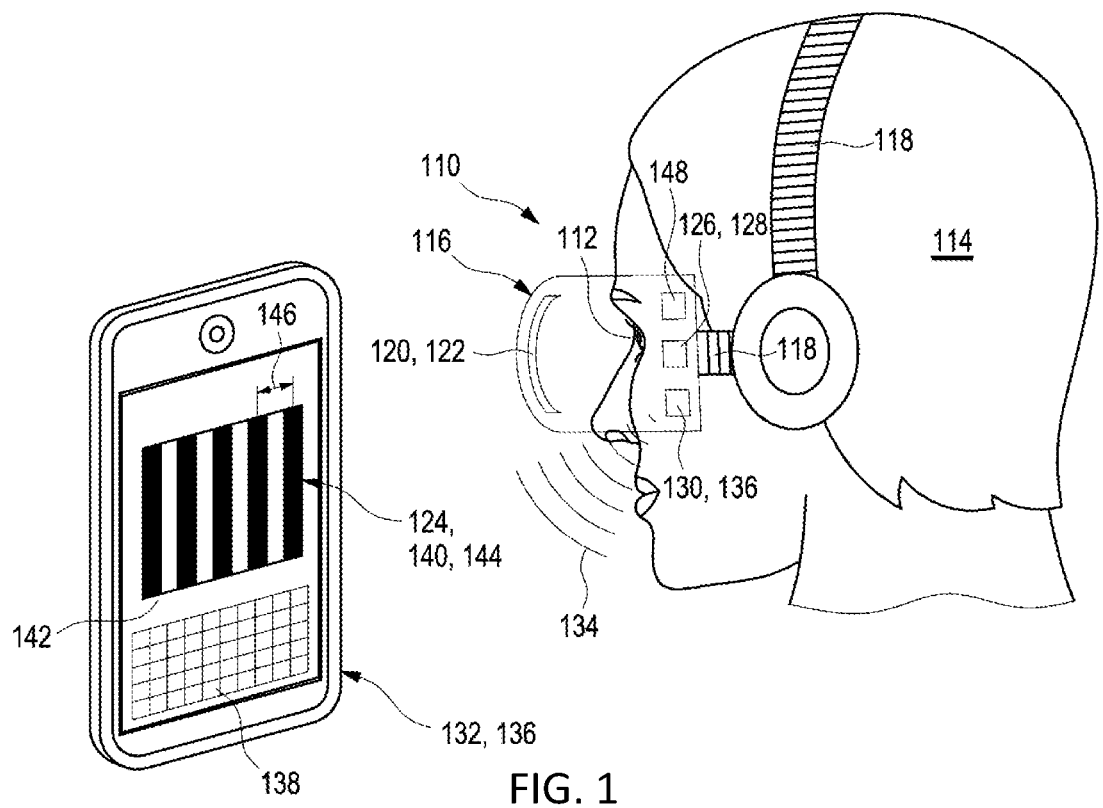
FIG. 1 illustrates an exemplary embodiment of a device for determining a contrast sensitivity threshold of eyes of a user according to the present disclosure.

FIG. 1 illustrates an exemplary embodiment of a device 110 for determining a contrast sensitivity threshold of eyes 112 of a user 114. As schematically depicted there, the device 110 implements a virtual reality environment by comprising a virtual reality headset 116 which is wearable by the user 114 by using one or more mounting elements 118. However, other kinds of fastening elements apart from the mounting elements 118 as displayed there are also feasible. In an alternative version (not depicted here) smart glasses as described above in more detail may be used instead of the virtual reality headset 116. In a further alternative version (not depicted here) a mobile communication device, in particular the smartphone 132 as described below, may be used for implementing the virtual reality environment.

Further, the virtual reality headset 116 comprises a screen 120 in form of a head mounted display 122 which is designated for displaying a stimulus 124 which is designed for eliciting movements of the eyes 112 of the user 114. In order to be able to perform the method according to the present disclosure, the stimulus 124 is designated for eliciting an optokinetic nystagmus in the eyes 112 of the user 114. As already mentioned above, the optokinetic nystagmus or "OKN" refers to a reflexive movement of the eyes 112 of the user 114 being generated as a response to a homogeneous optic flow, wherein involuntary slow pursuit movements alternate with saccadic quick phases.

Further, the virtual reality headset 116 comprises an eye tracker 126, wherein the eye tracker 126 is designated for recording a movement of the eyes 112 of the user 114. As schematically depicted in FIG. 1, a tracking device 128 can be mounted on the mounting elements 118 at each side of the eye in order to record the movement of each eye 112 of the user 114 individually. Herein, eye tracker 126 can be operated with a sampling rate of 100 Hz to 500 Hz, such as 250 Hz.

Further, the virtual reality headset 116 comprises a communication device 130 which is designated for communicating with a mobile communication device, in particular with a smartphone 132, preferably by using Wi-Fi or a Bluetooth connectivity 134. However, other kinds of mobile communication devices and/or connectivities may also be feasible. In the embodiment shown in FIG. 1, the communication device 130 and the smartphone 132 are combined in a fashion that they together form an evaluation unit 136 which is designated for determining the desired contrast sensitivity threshold of the eyes 112 of the user 114 by performing the method according to the present disclosure as described elsewhere herein. However, other kinds of evaluation units are conceivable, such as by integrating the evaluation unit 136 together with the screen 120 and the eye tracker 126 into the virtual reality headset 116. As further illustrated, the smartphone 132 comprises a virtual keyboard 138 for manual responses of the user 114.

Further in the virtual reality environment of FIG. 1, an OKN drum 140 is used for providing the stimulus 124. According to the embodiment as depicted in FIG. 1, the OKN drum 140 can be seen by the user 114 on the screen 120 of the virtual reality headset 116. For illustrative purposes only, the OKN drum 140 is, additionally, illustrated on a screen 142 of the smartphone 132. The OKN drum 140 as used herein refers to a cylinder having a large radius of two meters comprising a moving black and white stripe pattern 144 of a square-wave grating at its surface. Herein, the large radius of the cylinder was chosen in order to minimize a perspective-induced increase of a spatial frequency 146 in a periphery of a visual field of the user 114. In accordance with the present disclosure, the OKN drum 140 may, preferably, be presented as virtual reality to the user 114, whereby an image of the moving OKN drum 140 may be presented to the user. As a result thereof, the pattern 144 of the OKN drum 140 filled the full visual field of the user 114.

Further, the width of the black and white stripes can be defined freely in order to change the spatial frequency 146 of the pattern 144 during the performance of the method according to the present disclosure. By way of example, the spatial frequency 146 was selected as one of three different values comprising 0.25 cycles per degree (cpd), 0.5 cpd, and 0.75 cpd, based on Waddington et al, see above. However, less, further or other values may also be used for the spatial frequency 146. Further, the rotation of the OKN drum 140 can be set to a pre-determined velocity and direction. Herein, the velocity for the OKN drum 140 was set to a speed of 10 degree/sec based on Waddington et al, see above. However, other values for the velocity for the OKN drum 140 may also be feasible. For this purpose, the drum can be rotated clockwise and then anticlockwise in a manner that a horizontal motion of the pattern 144 is obtained, whereinafter the same rotation can be repeated around a further axis of the OKN drum 140, thereby generating a vertical motion of the pattern 144.

Contrast modulation can, preferably, be implemented as screen effect on the head mounted display 122. By way of example, the contrast was selected from one of four different values comprising 0.42%, 0.85%, 1.7%, and 10%. Herein, less, further or other values may also be used for the contrast. However, an absolute value for the contrast which is shown in the head mounted display 122 is, generally, not known. Consequently, the contrast sensitivity threshold can be determined either as a relative comparison between different contrast sensitivity thresholds or as an absolute contrast sensitivity threshold by, additionally, measuring a luminance level of the stimulus 124 in the screen 120, preferably by using a luminance sensor 148 further comprised by the virtual reality headset 116.

Figure 2:
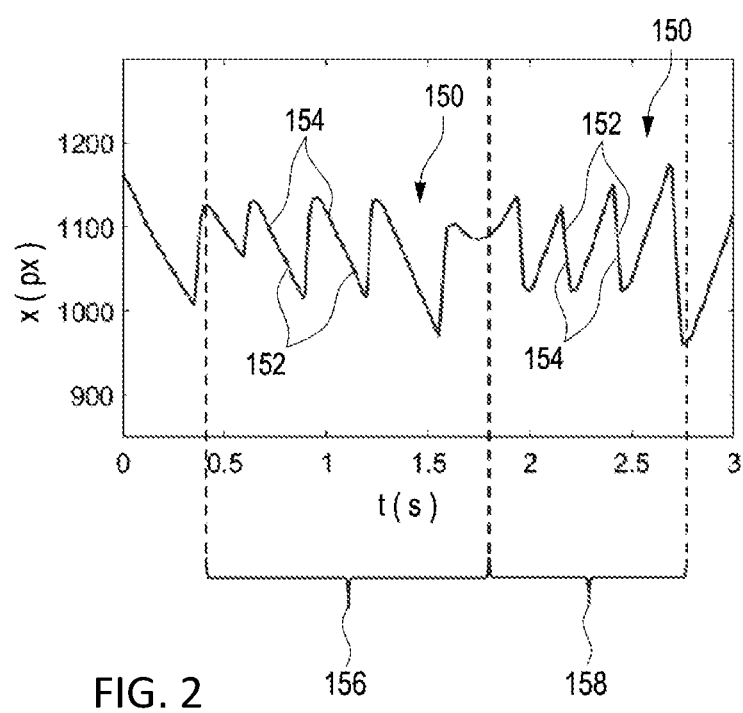
FIG. 2 illustrates exemplary experiment results from a contrast sensitivity test in accordance with the present disclosure, displaying prominently expressed slow pursuit movements and saccadic quick phases of an optokinetic nystagmus.

FIG. 2 illustrates exemplary experiment results which are obtained in a contrast sensitivity test in accordance with the present disclosure by eliciting an optokinetic nystagmus 150 in the eyes 112 of the user 114. As depicted there, involuntary slow pursuit movements 152 which alternate with saccadic quick phases 154 of the optokinetic nystagmus 150 are prominently visible. The experiment results are displayed on a diagram showing a point x of regard of the horizontal eye position in pixels px as a function of time t in seconds s. Herein, the direction of the slow pursuit movements 152 indicates the movement direction of the black and white stripe pattern 144. As further illustrated there, the horizontal eye position upon viewing the pattern 144 which moves at 10 degrees/sec changes a direction of the movement of the optokinetic nystagmus 150 after every 1.5 seconds, thereby resulting in an OKN movement to the left 156 and an OKN movement to the right 158.

Figure 3:
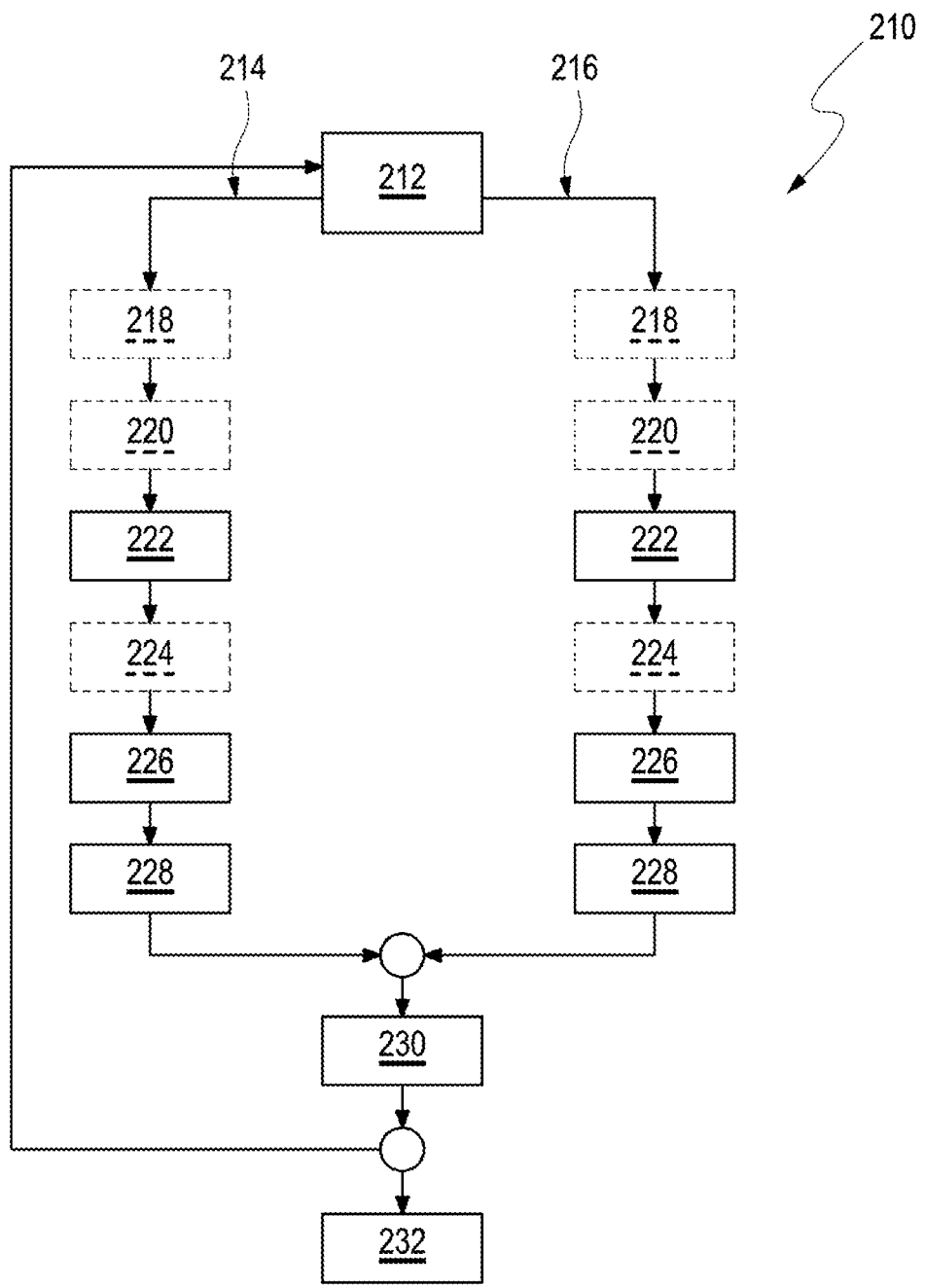
FIG. 3 illustrates an exemplary embodiment of a method for determining a contrast sensitivity threshold of eyes of a user according to the present disclosure.

FIG. 3 schematically illustrates an exemplary embodiment of a method 210 for determining the contrast sensitivity threshold of the eyes 112 of the user 114 according to the present disclosure.

In a providing step 212, a dataset of track data is provided in accordance with step a), wherein the track data comprise data of movements of the eye 112 of the user 114, wherein the movements of the eye 112 of the user 114 are stimulated by the stimulus 124 which is designated for eliciting the optokinetic nystagmus 150 in the eyes 112 of the user 114. Herein, the track data are related to particular visual parameters of the pattern 144, wherein the particular visual parameters may comprise the particular contrast and the particular spatial frequency 146 of the stimulus 124 as described above in more detail. Specifically, eye-tracking data can be stored in addition to frame-by-frame info on the rotation direction of the OKN drum 140 and the corresponding visual parameters of the pattern 144 on the OKN drum 140. In addition, synchronization markers being related to a change of direction of the rotation of the OKN drum 140 in the eye-tracking data may allow temporal matching of the eye-tracking data and the visual parameters of the pattern 144. Thus, by using binocular gaze data in arbitrary coordinates together with corresponding time stamps, data items can be formed, wherein each data item comprises a positional value of the position of the eye 112 of the user 114, a related temporal value and the corresponding visual parameters of the pattern 144. Herein, the track data can, preferably, be split into different phases according to the contrast and the spatial frequency 146 of the stimulus 124, thus allowing processing each phase separately. However, other kinds of processing may also be feasible.

In the exemplary embodiment as illustrated in FIG. 3, horizontal OKN 214 and vertical OKN 216 are analyzed individually. Herein, the order of the following steps as indicated below may be preferred; however, a different order may also be feasible.

In an optional filtering step 218, a saccade filter can, preferably, be applied in order to remove the saccadic quick phases 154 from the dataset of track data with an intention to analyze the slow pursuit movements 152 of the optokinetic nystagmus 150 in the eyes 112 of the user 114 exclusively. For this purpose, a known saccade filter, such as the saccade filter proposed by R. Kliegl, see above, may, preferably, be used. However, further kinds of saccade filters may also be applicable.

In an optional smoothing step 220, data was smoothed using a smoothing filter. For this purpose, a Savitzky-Golay filter may be preferred. However, other kinds of smoothing filters may also be feasible.

In an estimating step 222, the respective velocity component of the movement of the eye 112 of the user 114 is estimated according to step b) from the track data for the contrast and the spatial frequency 146 of the stimulus 124, wherein in the preferred embodiment of FIG. 3, the estimation step 222 is performed separately for the horizontal OKN 214 and for the vertical OKN 216, respectively.

In an exemplary embodiment of the present method 210, the stimulus 124 can exhibit a first direction of motion and a second direction of motion being opposite to the first direction of motion. Thus, in an optional merging step 224, data related to the opposite motion of the stimulus 124 can be inverted and, subsequently, merged with the data related to the first motion of the stimulus 124.

In a comparing step 226, the velocity component of the eye movement for the track data is compared with a velocity threshold. The velocity threshold is introduced in order to separate the slow pursuit movements 152 from residual eye movements of the eye 112 of the user 114. In the embodiment in which the saccadic quick phases 154 have been removed from the track data already during the filtering step 218, the slow pursuit movements 152 are assumed to be the fastest movement component.

In the exemplary embodiment of FIG. 3, the comparing step 226 is performed separately for the horizontal OKN 214 and for the vertical OKN 216, respectively. In this embodiment, a separate horizontal velocity threshold can be used in the comparing step 226 for the horizontal eye movement, and a separate vertical velocity threshold can, further, be used the comparing step 226 for the vertical eye movement. Herein, a horizontal velocity threshold of 13 px/s and a vertical velocity threshold of 5 px/s, respectively, which are optimized for the particular eye tracker 126 being used for recording the track data before step a), can be applied in the present comparing step 226. However, for a different eye tracker 126, different values for the horizontal velocity threshold and the vertical velocity threshold may be applicable.

In a further comparing step 228 a fraction of the track data which exceed the velocity threshold with a fractional threshold for the dataset is derived. Herein, a fractional threshold of 48% which is optimized for the particular eye tracker 126 being used for recording the track data before step a), can be used in the further comparing step 228. However, for a different eye tracker 126, a different value for the fractional threshold may be applicable. In the preferred embodiment of FIG. 3, the further comparing step 228 is performed separately for the horizontal OKN 214 and for the vertical OKN 216, respectively. If a higher fraction of the dataset of track data than the fractional threshold showed eye movement velocities which can be labeled as slow pursuit movements 152, the corresponding dataset of track data can be classified as eliciting the optokinetic nystagmus 150 at the particular contrast of the stimulus 124 in a binary decision. In contrast hereto, if a lower fraction of the dataset of track data than the fractional threshold showed eye movement velocities which can be labeled as slow pursuit movements 152, the corresponding dataset of track data cannot be classified as eliciting the optokinetic nystagmus 150 at the particular contrast of the stimulus 124 in the binary decision.

In the exemplary embodiment of FIG. 3, the binary decision is taken separately for the horizontal OKN 214 and for the vertical OKN 216, respectively. Thus, a final criterion 230 for an occurrence of the optokinetic nystagmus 150 at the particular contrast of the stimulus 124 is met if the binary decision classifies the dataset of track data as eliciting the optokinetic nystagmus 150 either for the horizontal OKN 214 or for the vertical OKN 216.

As further schematically indicated in FIG. 3, the preceding steps 212 to 228 are repeated for further particular visual parameters of the pattern 144, wherein the further particular visual parameters may comprise a further particular contrast and a further particular spatial frequency 146 of the stimulus 124. As indicated above, the spatial frequency 146 can, by way of example, be selected from three different values of 0.25 cycles per degree (cpd), 0.5 cpd, and 0.75 cpd, based on Waddington et al, see above. Similarly, the contrast can be selected from four different values of 0.42%, 0.85%, 1.7%, and 10%. However, less, further, or other values may also be used herein. By combining each value being selected for the spatial frequency 146 and/or for the contrast, 12 different scenes can be obtained in this manner, wherein the preceding steps are individually performed for each different scene.

Finally, typically after having individually performed the preceding steps for each selected scene, the contrast sensitivity threshold of the eyes 112 of the user 114 can be determined in a determining step 232 as described elsewhere in this document.

The at least one velocity threshold and the fractional threshold can be determined based on a ground truth. Herein, the ground truth can be generated by a visual inspection of the track data of a plurality of users 114. For this purpose, the track data of each eye 112 of each user 114, the direction of the movement of each eye 112 of each user 114 as well as the corresponding contrast and the spatial frequency 146 of the OKN drum 140 can be individually rated according to a two-step scale into categories: "no OKN" or "rather no OKN," in contrast to "OKN, or "rather OKN." The plurality of the users 114 can be randomly selected in order to estimate the parameters in this manner. Thereafter, the at least one velocity threshold and the fractional threshold can be optimized to fit the ground truth in these users 114. Afterwards, the values for the at least one velocity threshold and the fractional threshold can applied to further users 114 for validating purposes. Thus, in order to determine an optimized value for the velocity threshold, specifically for the horizontal velocity threshold and for the vertical velocity threshold, as well as an optimized value for the fractional threshold, the method 210 of FIG. 3 can be performed for various users 114, hereby using the same eye tracker 126.

In experiments the optimization of the at least one velocity threshold and the fractional threshold resulted in a horizontal velocity threshold of 13 px/s and a vertical velocity threshold of 5 px/s together with a fractional threshold 240 of 48%. When pooling data from all participants and all datasets for the horizontal velocity threshold of 13 px/s and evaluating the distribution of the occurring fractions of the optokinetic nystagmus 150 in the eyes 112 of the user 114, a bimodal distribution 242 becomes obvious which confirms an existence of a first set of measurements 244 without the occurrence of the optokinetic nystagmus 150 as well as a second set of measurements 246 with the occurrence of the optokinetic nystagmus 150 which are separated by the fractional threshold 240 of 48%.

Figure 4:
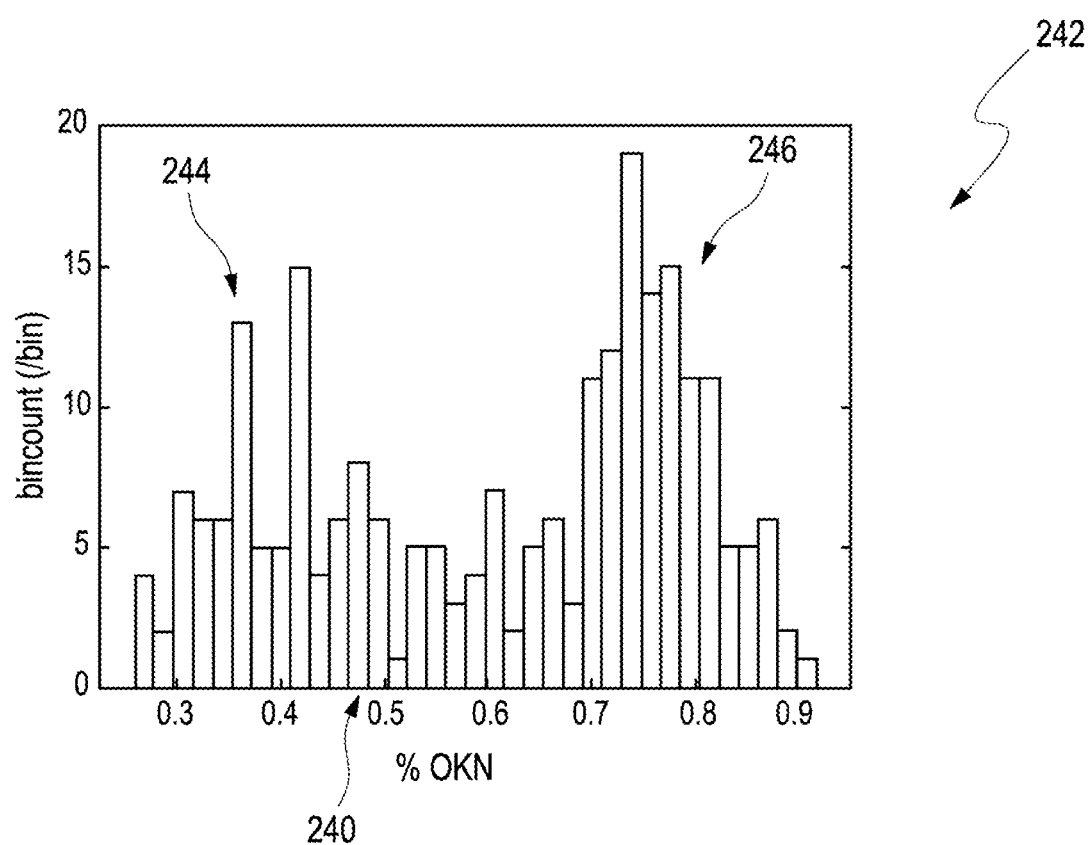
FIG. 4 illustrates a bimodal distribution with respect to resulting % OKN responses of horizontal OKN data from all spatial frequencies after application of a velocity threshold, thereby confirming the fractional threshold.

FIG. 4 illustrates the bimodal distribution 242 of the pooled horizontal velocity data by displaying resulting fractional responses of the horizontal OKN data from all spatial frequencies after application of a median velocity threshold of 13 px/s. Herein, the bimodal distribution 242 is clearly visible indicating the first set of measurements 244, wherein the optokinetic nystagmus 150 is rather not elicited, with a peak at approx. 0.35% OKN, and the second set of measurements 246, wherein the optokinetic nystagmus 150 is elicited with a peak at approx. 0.75% OKN. This distribution confirms the selected fractional threshold 240 of 48%.

Using the horizontal velocity threshold of 13 px/s, the vertical velocity threshold of 5 px/s, and the fractional threshold 240 of 48% for a validation process, all 60 validation datasets of the five users 114 were correctly categorized horizontally while 52 out of 60 validation datasets of the five users 114 were correctly categorized vertically, leading to a correct classification of 53 out of 60 datasets in the experiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS 110 device
112 eyes
114 user
116 virtual reality headset
118 mounting elements
120 screen
122 head mounted display
124 stimulus
126 eye tracker
128 light-house
130 communication device
132 smartphone
134 Wi-Fi or Bluetooth connectivity 136 evaluation unit
138 virtual keyboard
140 OKN drum
142 screen
144 pattern
146 spatial frequency
148 luminance sensor
150 optokinetic nystagmus (OKN)
152 slow pursuit movements
154 saccadic quick phases
156 OKN movement to the left
158 OKN movement to the right
210 method
212 providing step
214 horizontal OKN
216 vertical OKN
218 filtering step
220 smoothing step
222 estimation step
224 merging step
226 comparing step
228 further comparing step
230 final criterion
232 determining step
240 fractional threshold
242 bimodal distribution
244 first set of measurements
246 second set of measurements

The invention claimed is:

1. A method for determining a contrast sensitivity threshold of eyes of a user, the method comprising:
providing a dataset of track data, wherein the track data contains data of eye movements obtained by eliciting an optokinetic nystagmus in the eyes of the user by stimulating the eye movements with a stimulus, wherein the track data are related to a particular contrast and a particular spatial frequency of the stimulus;
estimating at least one velocity component of the eye movement from the track data for the particular contrast and the particular spatial frequency of the stimulus;
comparing the velocity component of the eye movement for the track data with a velocity threshold;
determining the contrast sensitivity threshold of the eyes of the user; and
further comparing a fraction of the track data which exceeds the velocity threshold with a fractional threshold for the dataset, wherein the fraction of the track data which exceeds the fractional threshold is classified as eliciting the optokinetic nystagmus at the particular contrast of the stimulus, and
wherein the contrast sensitivity threshold of the eyes of the user is determined by applying the velocity threshold and the fractional threshold.

2. The method according to claim 1, wherein the velocity threshold and the fractional threshold are independent from the user.

3. The method according to claim 1, wherein the velocity threshold and the fractional threshold are dependent from an eye tracker configured to record the track data.

4. The method according to claim 1, further comprising:
splitting the dataset into at least two subsets for the contrast and the spatial frequency of the stimulus; and
processing each of the at least two subsets separately.

5. The method according to claim 1, further comprising:
applying a saccade filter to remove track data from the dataset which refer to saccadic quick phases contained in the optokinetic nystagmus.

6. The method according to claim 1, wherein the dataset is smoothed.

7. The method according to claim 1, wherein the stimulus exerts a motion in at least one direction.

8. The method according to claim 7, further comprising:
presenting an optokinetic nystagmus (OKN) drum to the user; or
presenting an image of a moving OKN drum to the user as virtual reality by providing at least one of a virtual reality headset, an augmented reality overlay, or a mobile communication device.

9. The method according to claim 8, wherein a different stimulus is used to exert the motion in a horizontal direction and in a vertical direction, respectively.

10. A method for determining a contrast sensitivity threshold of eyes of a user, the method comprising:
providing a dataset of track data, wherein the track data contains data of eye movements obtained by eliciting an optokinetic nystagmus in the eyes of the user by stimulating the eye movements with a stimulus, wherein the track data are related to a particular contrast and a particular spatial frequency of the stimulus;
estimating at least one velocity component of the eye movement from the track data for the particular contrast and the particular spatial frequency of the stimulus;
comparing the velocity component of the eye movement for the track data with a velocity threshold;
determining the contrast sensitivity threshold of the eyes of the user;
further comparing a fraction of the track data which exceeds the velocity threshold with a fractional threshold for the dataset, wherein the fraction of the track data which exceeds the fractional threshold is classified as eliciting the optokinetic nystagmus at the particular contrast of the stimulus, and
wherein the contrast sensitivity threshold of the eyes of the user is determined by applying the velocity threshold and the fractional threshold,
wherein the stimulus exerts a motion in at least one direction;
presenting an optokinetic nystagmus (OKN) drum to the user; or
presenting an image of a moving OKN drum to the user as virtual reality by providing at least one of a virtual reality headset, an augmented reality overlay, or a mobile communication device;
wherein a different stimulus is used to exert the motion in a horizontal direction and in a vertical direction, respectively, and
wherein the velocity component is estimated separately for a horizontal eye movement and a vertical eye movement, wherein the horizontal eye movement follows the motion of the stimulus in the horizontal direction, and wherein the vertical eye movement follows the motion of the stimulus in the vertical direction.

11. The method according to claim 10, wherein a horizontal velocity threshold is used for the horizontal eye movement, and wherein a vertical velocity threshold is used for the vertical eye movement.

12. The method according to claim 10, wherein the track data being related to an opposite motion of the stimulus are inverted and merged.

13. The method according to claim 10, wherein the dataset is classified as eliciting the optokinetic nystagmus if the dataset has been classified as eliciting the optokinetic nystagmus for the horizontal eye movement or for the vertical eye movement.

14. A method for determining a contrast sensitivity threshold of eyes of a user, the method comprising:
providing a dataset of track data, wherein the track data contains data of eye movements obtained by eliciting an optokinetic nystagmus in the eyes of the user by stimulating the eye movements with a stimulus, wherein the track data are related to a particular contrast and a particular spatial frequency of the stimulus;
estimating at least one velocity component of the eye movement from the track data for the particular contrast and the particular spatial frequency of the stimulus;
comparing the velocity component of the eye movement for the track data with a velocity threshold;
determining the contrast sensitivity threshold of the eyes of the user;
further comparing a fraction of the track data which exceed the velocity threshold with a fractional threshold for the dataset, wherein the fraction of the track data which exceeds the fractional threshold is classified as eliciting the optokinetic nystagmus at the particular contrast of the stimulus, and
wherein the contrast sensitivity threshold of the eyes of the user is determined by applying the velocity threshold and the fractional threshold; and
estimating the velocity threshold and the fractional threshold in a calibration process in which the contrast sensitivity is determined in a same manner with at least two different users, wherein same contrasts and same spatial frequencies of a same stimulus are utilized.

15. The method according to claim 1, further comprising:
measuring a luminance level of the stimulus, wherein the contrast sensitivity threshold is determined as an absolute contrast sensitivity threshold by considering a measured value for the luminance level of the stimulus.

16. A non-transitory computer readable storage medium storing executable instructions for performing a method for determining a contrast sensitivity threshold of eyes of a user, the method comprising:
providing a dataset of track data, wherein the track data contains data of eye movements obtained by eliciting an optokinetic nystagmus in the eyes of the user by stimulating the eye movements with a stimulus, wherein the track data are related to a particular contrast and a particular spatial frequency of the stimulus;
estimating at least one velocity component of the eye movement from the track data for the particular contrast and the particular spatial frequency of the stimulus;
comparing the velocity component of the eye movement for the track data with a velocity threshold;
determining the contrast sensitivity threshold of the eyes of the user; and
further comparing a fraction of the track data which exceed the velocity threshold with a fractional threshold for the dataset, wherein the fraction of the track data which exceeds the fractional threshold is classified as eliciting the optokinetic nystagmus at the particular contrast of the stimulus, and
wherein the contrast sensitivity threshold of the eyes of the user is determined by applying the velocity threshold and the fractional threshold.

17. A device for determining a contrast sensitivity threshold of eyes of a user, the device comprising:
a screen configured to display a stimulus, wherein the stimulus is designated for eliciting an optokinetic nystagmus in the eyes of the user;
an eye tracker configured to record eye movements of the eyes of the user; and
an evaluation unit, wherein the evaluation unit is configured to:
provide a dataset of track data, wherein the track data contains data of the eye movements, wherein the eye movements are stimulated by a stimulus which is configured to elicit an optokinetic nystagmus in the eyes of the user, wherein the track data are related to a particular contrast and a particular spatial frequency of the stimulus;
estimate at least one velocity component of the eye movement from the track data for the particular contrast and the particular spatial frequency of the stimulus;
compare the velocity component of the eye movement for the track data with a velocity threshold;
determine the contrast sensitivity threshold of the eyes of the user; and
further compare a fraction of the track data which exceed the velocity threshold with a fractional threshold for the dataset, wherein the fraction of the track data which exceeds the fractional threshold is classified as eliciting the optokinetic nystagmus at the particular contrast of the stimulus, and
wherein the contrast sensitivity threshold of the eyes of the user is determined by applying the velocity threshold and the fractional threshold.

18. The device according to claim 17, wherein the screen and the eye tracker are integrated in a virtual reality headset, in smart glasses, or in a mobile communication device, and wherein the evaluation unit is contained by at least one of the virtual reality headset and the mobile communication device.

* * * * *

UNITED STATES PATENT AND TRADEMARK OFFICE
CERTIFICATE OF CORRECTION

PATENT NO. : 11,529,049 B2
APPLICATION NO. : 17/555692
DATED : December 20, 2022
INVENTOR(S) : Katharina Rifai, Siegfried Wahl and Sophia Tatiyosyan It is certified that error appears in the above-identified patent and that said Letters Patent is hereby corrected as shown below:

In the Specification

Column 9, Line 33, change "distance Do" to -- distance $D_\Theta$ --.

Column 9, Line 36, change "distance Do, a ratio Co" to -- distance $D_\Theta$, a ratio $C_\Theta$ --.

Column 9, Line 39, change "ratio Co" to -- ratio $C_\Theta$ --.

Signed and Sealed this
Thirty-first Day of January, 2023

Katherine Kelly Vidal
*Director of the United States Patent and Trademark Office*